(12) United States Patent
Møllgaard et al.

(10) Patent No.: US 9,365,819 B2
(45) Date of Patent: Jun. 14, 2016

(54) **PROCESS FOR CULTURING *LACTOCOCCUS* BACTERIA**

(75) Inventors: Henrik Møllgaard, Lyngby (DK);
Henrik Rømer, Frederiksberg (DK);
Asger Geppel, Gentofte (DK)

(73) Assignee: Chr. Hansen A/S, Horsholm (DK)

( * ) Notice: Subject to any disclaimer, the term of this patent is extended or adjusted under 35 U.S.C. 154(b) by 1842 days.

(21) Appl. No.: 11/916,339

(22) PCT Filed: Jun. 16, 2006

(86) PCT No.: PCT/DK2006/050024
§ 371 (c)(1),
(2), (4) Date: Jan. 23, 2008

(87) PCT Pub. No.: WO2006/133718
PCT Pub. Date: Dec. 21, 2006

(65) Prior Publication Data
US 2008/0227177 A1    Sep. 18, 2008

(30) Foreign Application Priority Data

Jun. 17, 2005 (DK) .................................. 2005 00892
Jul. 15, 2005 (DK) .................................. 2005 01053

(51) Int. Cl.
*C12N 1/20* (2006.01)

(52) U.S. Cl.
CPC ...................................... *C12N 1/20* (2013.01)

(58) Field of Classification Search
None
See application file for complete search history.

(56) References Cited

U.S. PATENT DOCUMENTS

| 6,689,601 | B2 | 2/2004 | Koffas et al. |
| 2005/0032196 | A1 | 2/2005 | Duwat et al. |

FOREIGN PATENT DOCUMENTS

| EP | 1 241 248 A | 9/2002 |
| EP | 1 241 248 A1 | 9/2002 |
| WO | WO 01/60974 A2 | 8/2001 |
| WO | WO 03/089625 A2 | 10/2003 |

OTHER PUBLICATIONS

Ovchinnikova et al., Journal of Peptide Science, vol. 9, pp. 817-826 (2003).*
Molnar et al. (Milchwissenschaft Y. 2005, vol. 60, No. 4, pp. 380-382).*
Duwat et al., Journal of Bacteriology, vol. 183, pp. 4509-4516, Aug. 2001.*
Main brochure from the company Norferm A/S: "A New High Quality Single Cell Protein Based on Natural Gas", www.Norferm.no.

* cited by examiner

*Primary Examiner* — Irene Marx
(74) *Attorney, Agent, or Firm* — Foley & Lardner LLP

(57) ABSTRACT

This invention relates to an improved process for culturing bacteria of the family Streptococcaceae (such as of the genus *lactococcus*), a medium for culturing the bacteria, and the obtained bacteria cells.

18 Claims, 1 Drawing Sheet

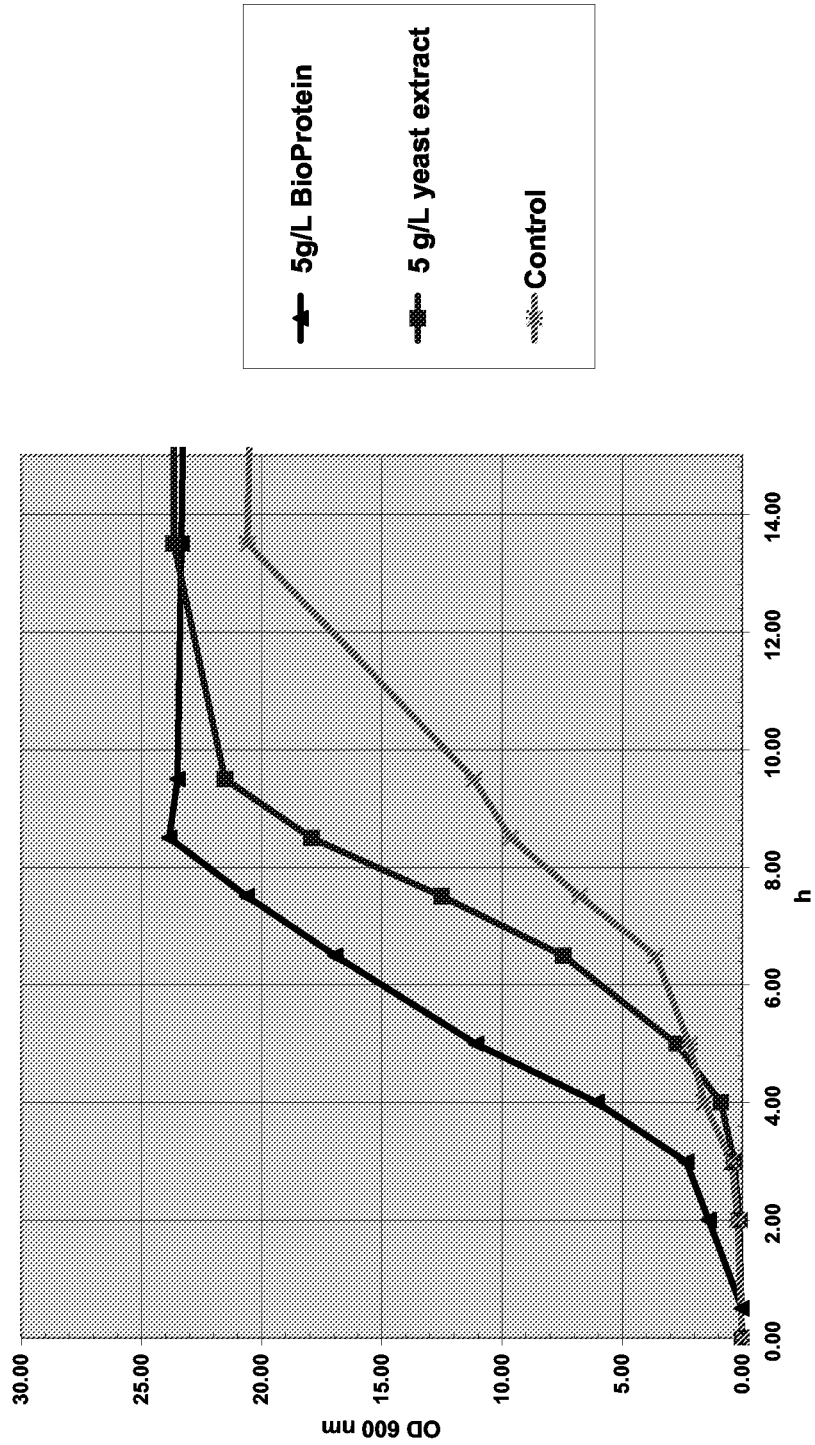

PROCESS FOR CULTURING *LACTOCOCCUS* BACTERIA

FIELD OF INVENTION

This invention relates to an improved process for culturing bacteria of the family Streptococcaceae, a medium for culturing the bacteria, and the obtained bacteria cells.

BACKGROUND OF INVENTION

Bacteria of the family Streptococcaceae (which are lactic acid producing bacteria) have previously been propagated in different media, such as media containing yeast extract. US patent application 20050032196 [INRA, France] discloses the propagation of lactic acid bacteria of the genus *Lactococcus lactis* (which belongs to the family Streptococcaceae) in the standard laboratory medium M17 which contains peptone, lactose and yeast extract.

There is still a need for providing improved media for propagating lactic acid bacteria of the family Streptococcaceae, which media can result in a higher yield of cells, and of cells having an improved viability, thereby reducing the cost of production.

SUMMARY OF INVENTION

The present inventors have found that when cells of the family Streptococcaceae, especially of the genus *Lactococcus*, are cultured aerobically in a medium containing biomass ("single cell protein" or an autolysate) obtained from a methanotrophic/methylotrophic microorganism of the species *Methylococcus capsulatus*, it is possible to obtain a surprisingly fast growth rate of the cells, a surprisingly fast adaptation of the cells to the medium at the start of the culturing, and a surprisingly high concentration of cells as compared to the concentration of cells obtained when a similar medium containing yeast extract is used.

In accordance with this finding, the above objective has been solved by the present invention, which in its broadest scope provides a process for culturing a bacterium of the family Streptococcaceae in a nutrient medium, which comprises biomass, obtained from a methylotrophic and/or methanotrophic microorganism.

WO 03/089625 A2 [Norferm Da, Norway] discloses a method for culturing *Lactobacillus plantarum* and *Lactobacillus acidophilus* (both of the family *Lactobacillaceae*) in a medium containing biomass of *Methylococcus capsulatus* NCIMB 11132, *Ralstonia* sp. NCIMB 13287, *Aneurinibacillus* sp. NCIMB 13288 and *Brevibacterium agri* NCIMB 13289 (biomass produced as described in WO 01/60974). From the growth tests (example 6) it can be concluded that replacement of yeast extract with the same amount of BP (biomass of methanotrophic bacteria) in the MRS standard medium does not result in an improvement in the number of viable cells (table 7 and 8; comparing row 2 with row 5 in both tables). WO 03/089625 A2 is silent about culturing bacteria of the family Streptococcaceae.

In contrast to the above findings for *Lactobacillus*, the present inventors have surprisingly found that replacement of yeast extract with the same amount of BP when culturing a strain of *Lactococcus* results in an surprising improvement, such as in growth rate, see example 1 and FIG. 1.

DETAILED DISCLOSURE

In a first aspect, the present invention pertains to a process for preparing (or propagating) a bacterial culture, including a lactic acid bacteria (LAB) culture (such as a starter culture or a probiotic culture), comprising culturing at least one strain of the family Streptococcaceae (such as of the following genera: *Leuconostoc, Enterococcus*, and *Lactococcus*) in a nutrient medium which comprises biomass obtained from a methylotrophic and/or methanotrophic microorganism. In other words, the invention pertains to a process for culturing (or propagating) a strain of the family Streptococcaceae, said process comprises culturing in a nutrient medium as defined above, and a process for culturing (or propagating) a bacterial strain of the family Streptococcaceae, comprising inoculating the bacteria in a nutrient medium as defined above. Especially, the invention pertains to a process for increasing the growth rate, and/or improving the viability of the Streptococcaceae cells.

The nature of the biomass is not crucial, it can be in the form of cell material, such as whole cells; a lysate of the microorganism, such as an autolysate, hydrolysate or homogenizate; an extract of the microorganism, such as the water soluble fraction of the lysed cell; or a mixture of any of these. The cell material, lysate or extract may optionally be treated, e.g. hydrolyzed, dried and/or filtrated. The advantageous effect of the biomass is anticipated to be present even if a small amount of the biomass is added to the nutrient medium, but it is preferred that the biomass, especially the extract or lysate, is present in an amount of 0.1 to 50 g/L nutrient medium, such as in an amount of 1-40 g/L; 3-30 g/L; 2-10 g/L; 0.1-10 g/L; 1-5 g/L or 5-15 g/L.

In an interesting embodiment, the methylotrophic and/or methanotrophic microorganism has been cultured on a substrate comprising as the primary carbon and/or energy source a compound which is partly (compared to a carbohydrate) or fully reduced (or which contains carbon in a lower oxidation state than in carbon dioxide), such as on a substrate that, as the primary carbon and/or energy source, contains a compound having a ratio C/C+O (no. of carbon atoms/{no. of carbon atoms+no. of oxygen atoms}) in the range 0.6-1.0, such as in the range 0.8-1.0 or in the range 0.9-1.0. The substrate can comprise a compound selected from: an alkane, preferably a C1-C6 alkane, such as methane, ethane, propane or n-butane; an alkanol, preferably a C1-C6 alkanol, such as ethanol or methanol; and an alkene, preferably a C2-C6 alkene, such ethylene, propylene, or 1-butylene. Conveniently, the methylotrophic and/or methanotrophic microorganisms have been produced by fermentation on a substrate containing a hydrocarbon fraction or containing an alkane containing gas, such as natural gas. It is anticipated that some microorganisms (not being classified as a methylotrophic and/or methanotrophic) are able to utilize a compound as defined above as a carbon source. The biomass of such a microorganism (e.g. when cultured on a substrate as defined above) may be used in the process for preparing a bacterial culture. Such a process is an embodiment of the present invention.

In a preferred embodiment of the process of the invention, the methylotrophic and/or methanotrophic microorganism is a *Methylococcus* species, including *Methylococcus capsulatus* (such as NCIMB 11132). Other microorganisms that might be used include: *Methylomonas* species, such as *M. rubra, M. methanica, M. gracilis, M. albus, M. clara, M. agile; Methylococcus* species, such as *M. luteus, M. ucrainicus, M. thermophilus; Methylosinus* species, such as *M. sporium, M. trichosporium; Methylocystis* species, such as *M. fistulosa* and *M. parvus, Methylobacter* species, such as *M. whitterbury, M. lutes*.

In addition to the biomass of the methylotrophic and/or methanotrophic microorganism, the nutrient medium may contain biomass (such as whole cells, an extract or a lysate)

obtained from at least one of the following species: *Ralstonia* sp. (inc. NCIMB 13287), *Aneurinibacillus* sp. (inc. NCIMB 13288) and *Brevibacterium* sp., such as *B. agri* (inc. NCIMB 13289). It is presently preferred that the biomass is "BioProtein" (essentially spray-dried autolysed *Methylococcus capsulatus*) obtainable from Norfern AS, Norway. The biomass can be produced as disclosed in WO 01/60974, but it is anticipated that also a fraction of the *Methylococcus* biomass can be used in the process of the invention. Such a fraction may be a lysate wherein a component (e.g. a component which has an negative effect on the LAB or the yield of the process) has been removed.

The nutrient medium may comprise at least one further component, such as a carbohydrate (incl. lactose or glucose); and/or a complex component (such as yeast extract or a peptone); and/or a porphyrin source (such as blood or a fraction thereof, including heme and hemin); and/or a mineral salt.

In a preferred embodiment, the strain of the family Streptococcaceae belongs to a species selected from the group consisting of *Lactococcus* sp. (such as *Lactococcus lactis* subsp. *lactis* (including *biovar diacetylactis*) or *Lactococcus lactis* subsp. *cremoris*); *Leuconostoc* sp. (including *Leuconostoc mesenteroides*); and *Enterococcus* sp.

The physical parameters of the process of the invention is not anticipated to be critical, but it is presently preferred that the culturing is carried out under aeration, e.g. the culture is aerated so as to maintain an oxygen content, which is at least 2 micromoles per liter of culture medium. The temperature is preferably in the range of 20-45 degrees C., such as in the range of 25-40 or 30-35 degrees C.

The process of the invention may further comprise at least one steps selected from: harvesting the bacteria, preferably between 5 and 24 hours after the start of the culturing, such as by centrifugation or filtration; storing the harvested bacteria, such as at approximately 1-5 degrees C; freezing or lyophilizing the harvested bacteria; storing the frozen or lyophilized bacteria; and packaging the harvested bacteria (optionally in frozen or lyophilized form).

In a second aspect, the invention pertains to a nutrient medium for propagating bacteria (including LAB) of the family Streptococcaceae, which medium is defined as above, such as a medium which contains whole cells, an extract or a lysate of a *Methylococcus* species, including *Methylococcus capsulatus*.

In a third aspect, the invention pertains to a process for preparing a LAB culture (including a starter culture) comprising culturing at least one strain of the genus *Lactococcus* under aeration in a nutrient medium of the invention.

In a fourth aspect, the invention pertains to a LAB culture (including a starter culture) obtained by the process of the invention, such as a culture of *Lactococcus lactis*, including *Lactococcus lactis* subspecies *lactis* and *cremoris*. The culture of the invention differs from the known cultures of the same species in that its cellular components are optimized for a high growth rate and a high viability, possible due to the culture containing specific components originating from the growth medium.

In a fifth aspect, the invention pertains to a method for preparing a fermented product, comprising inoculating a medium (such as milk or a crop) to be fermented with a lactic acid bacteria starter culture according to the invention. The prepared fermented product is also an aspect of the present invention.

In a further aspect, the invention pertains to the use of biomass obtained from a microorganism cultured on a substrate that, as the primary carbon and/or energy source, does not contain a carbohydrate; and/or
contains a compound having a ratio C/C+O (no. of carbon atoms/{no. of carbon atoms+no. of oxygen atoms}) in the range 0.6-1.0, such as in the range 0.8-1.0 or in the range 0.9-1.0; and/or
contains an alkane, preferably a C1-C6 alkane, such as methane, ethane, propane or butane; and/or
contains an alkanol, preferably a C1-C6 alkanol, such as ethanol or methanol; and/or
contains an alkene, preferably a C2-C6 alkene, such ethylene, propylene, or 1-butylene;

for the preparation of a medium for preparing/propagating bacteria (including LAB) of the family Streptococcaceae. In a preferred embodiment, the invention relates to the use of the biomass obtained from a *Methylococcus* species, including biomass from autolysed *Methylococcus capsulatus* cultured on a substrate as defined above, for the preparation of a medium for preparing/propagating lactic acid bacteria of the family Streptococcaceae, including the genus *Lactococcus*.

DEFINITIONS

In the present context the term "strain of the family Streptococcaceae" designates a bacterial strain of one of the following genera: *Streptococcus, Leuconostoc, Oenococcus, Pediococcus, Aerococcus, Gemella, Enterococcus*, and *Lactococcus*; all of which are facultative anaerobic, catalase-negative, fermentative, G+cocci. Examples of species included within this term are: *Enterococcus aerogenes, Enterococcus faecium, Lactococcus* (previously *Streptococcus*) *lactis, Lactococcus lactis* subsp. *lactis, Lactococcus lactis* subsp. *lactis biovar. diacetylactis, Lactococcus lactis* subsp. *diacetylactis* (previously *Streptococcus diacetylactis*), *Lactococcus lactis* subsp. *cremoris, Lactococcus acidophilus, Lactococcus cremoris, Leuconostoc carnosum, Leuconostoc citrivorum, Leuconostoc dextranicum, Leuconostoc mesenteroides* subsp. *cremoris, Leuconostoc pseudomesenteroides, Oenococcus oeni* (previously *Leuconostoc oenos*), *Pediococcus acidilactici, Pediococcus pentosaceus, Streptococcus salivarius* subsp. *thermophilus, Streptococcus cremoris, Streptococcus diacetylactis, Streptococcus durans, Streptococcus faecium, Streptococcus lactis* and *Streptococcus thermophilus* (previously *Streptococcus salivarius* subsp. *thermophilus*).

The term "carbon source" refers to a material containing at least one carbon atom which can be enzymatically converted into an intermediate for subsequent conversion into the desired carbon end-product. Exemplary carbon sources include biomass, starches, dextrins and carbohydrates.

The term "culture" is well known in the art, and includes a culture containing a single strain of a bacterium, or more than one bacterial strain. The term "starter culture" is well known in the art, and includes a bacterial culture that is suitable for use in e.g. dairies and agriculture (silage). The term "probiotic culture" is well known in the art and includes a culture of bacteria capable of passing the gastro-intestinal tract in an essentially viable and live form and optionally also being capable of stimulating the host's immune system.

The term "methylotrophic microorganism" includes microorganisms that can use, as substrates for growth, C1 compounds containing carbon in a lower oxidation state than in carbon dioxide (such as methanol, methylamine, and methane). The term "methanotrophic microorganism" includes microorganisms that can utilize the gas methane. Methanotrophic microorganisms are often considered to be a subset of methylotrophic microorganisms. Examples on methanotropic/methylothopic microorganisms are: *Methylomonas* species, such as *M. rubra, M. methanica, M. gracilis, M. albus, Methylomonas* 16a (US6689601B2), *M. clara, M. agile; Methylococcus* species, such as *M. luteus, M. ucrainicus, M. thermophilus, M. capsulatus; Methylosinus* species, such as *M. sporium, M. trichosporium; Methylocystis* species, such as *M. fistulosa* and *M. parvus, Methylobacter* species, such as *M. whitterbury, M. lutes*.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising", "having", "including" and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention. All references mentioned herein are hereby incorporated by reference herein in their entireties.

EXAMPLES

Example 1

Growth of *Lactococcus* in Media with Added Bioprotein

*Lactococcus lactis* strain CHCC2862 (obtainable from Chr. Hansen A/S, Denmark) was used to inoculate 1.5 L medium as specified below in a 2 L Applicon fermenter with pH and temperature control. The pH was controlled by addition of concentrated ammonia to 5.9. The temperature was constant at 34° C., and stirring was maintained at a high level at 1200 rpm in order to ensure efficient aeration from a 0.5 vvm air flow. The medium used was the standard growth medium M17 with extra added lactose (40 g/L) and Hemin (1 ppm) in order to enable extended growth (control medium).

Fermentations with the additions to the above medium as described in the following table were performed. BioProtein (essentially consisting of spray-dried autolysed *Methylococcus capsulatus* biomass) was obtained from Norferm AS (Norway), yeast extract was obtained from BioSpringer (no. 0207), and Hemin was obtained from Fluka (prod. no. 51280).

| Addition | Biomass measured as optical density (600 nm), hours after start | | | |
|---|---|---|---|---|
| | 2 | 5 | 8 | 15(end) |
| None (control) | 0 | 2 | 8 | 20 |
| Yeast extract (5 g/L) | 0 | 3 | 15 | 23 |
| BioProtein (5 g/L) | 2 | 11 | 22 | 23 |

Addition of BioProtein obviously is a large improvement. The improvement is significantly larger than the improvement obtained with addition of yeast extract, especially early in the fermentation. Further advantages of adding BioProtein are revealed from the growth curves (see FIG. 1), such as (i) the growth starts immediately, (ii) the growth rate is fast, (iii) the cells can be harvested early after the start of the culturing, and (iv) the final amount of biomass/number of viable cells is high.

In summary: The addition of Bioprotein is a very large improvement of the growth of *Lactococcus lactis*, both with respect to fermentation time and biomass yield.

Example 2

*Lactococcus lactis* strain CHCC2862 was used to inoculate 1.5 L medium as specified below in a 2 L Applicon fermenter with pH and temperature control. The pH was controlled by adding concentrated ammonia to 5.9. The temperature was constant at 34° C., and stirring was maintained at a high level at 1200 rpm in order to ensure efficient aeration from a 0.5 vvm air flow. The medium used was the standard growth medium M17 with extra added lactose (40 g/L) (control medium). Yeast extract or Bioprotein were added to the control medium as defined in the table.

| Medium | *Lactococcus lactis* |
|---|---|
| M17 + 40 g/L lactose (control) | |
| Control + Biospringer yeast extract (5 g/L) | + |
| Control + BioProtein (5 g/L) | ++ |

+: Growth somewhat better than the control
++: Growth significantly better than the control Example 3

Using the same conditions as in example 2, *Lactococcus cremoris* strain CHCC4462 (obtainable from Chr. Hansen A/S, Denmark) is propagated in the following media:

| Medium | *Lactococcus cremoris* |
|---|---|
| M17 + 40 g/L lactose (control) | |
| Control + Biospringer yeast extract (5 g/L) | + |
| Control + BioProtein (5 g/L) | ++ |

+: Growth somewhat better than the control
++: Growth significantly better than the control Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

REFERENCES

U.S. Pat. No. 6,689,601 B2
US 2005/0032196 A1
WO 03/089625 A2
WO 01/060974 A2

All references cited in this patent document are hereby incorporated herein in their entirety by reference.

The invention claimed is:

1. A process for preparing a bacteria culture, comprising culturing a *Lactococcus lactis* strain under aeration in a nutrient medium comprising a biomass of a methanotrophic *Methylococcus capsulatus* bacterium, wherein the biomass is selected from the group consisting of a hydrolysate of the *Methylococcus capsulatus* bacterium, a homogenate of the *Methylococcus capsulatus* bacterium, an autolysate of the *Methylococcus capsulatus* bacterium, and a water soluble extract of the *Methylococcus capsulatus* bacterium, and wherein the biomass is present in an amount of 5 to 40 g/l of the nutrient medium, thereby preparing a bacterial culture.

2. The process of claim 1, wherein the hydrolysate, homogenate, autolysate, or water soluble extract optionally is treated by hydrolysis, drying, filtration, or a combination thereof.

3. The process of claim 1, wherein the *Methylococcus capsulatus* bacterium is produced by culturing the bacterium on a substrate comprising as the primary carbon and/or energy source a compound which is partly or fully reduced.

4. The process of claim 3, wherein the substrate as the primary carbon and/or energy source contains a compound having a ratio of C/C+O in the range of 0.6-1.0.

5. The process of claim 1, wherein the *Methylococcus capsulatus* bacterium is produced by culturing the bacterium on a substrate comprising as the primary carbon source a compound selected from the group consisting of an alkane, an alkanol and an alkene.

6. The process of claim 1, wherein the *Methylococcus capsulatus* bacterium is produced by fermentation on a substrate containing a hydrocarbon fraction or containing an alkane containing gas.

7. The process of claim 1, wherein the nutrient medium further comprises biomass of a microorganism selected from at least one of *Ralstonia* sp, *Aneurinibacillus* sp. and *Brevibacterium*.

8. The process of claim 1, wherein the nutrient medium further comprises one or more selected from the group consisting of an additional carbon source, a yeast extract, a mineral salt, or a combination thereof.

9. The process of claim 1, wherein the *Lactococcus lactis* strain is selected from the group consisting of *Lactococcus lactis* subsp. *lactis*, *Lactococcus lactis* subsp. *lactis biovar. diacetylactis*, and *Lactococcus lactis* subsp. *cremoris*.

10. The process of claim 1, further comprising maintaining the oxygen content of the culture at a level of at least 2 micromoles per liter of culture medium.

11. The process of claim 1, further comprising harvesting the prepared bacteria culture.

12. The process of claim 4, wherein the alkane is a C1-C6 alkane selected from the group consisting of methane, ethane, propane and n-butane.

13. The process of claim 4, wherein the alkanol is a C1-C6 alkanol selected from the group consisting of ethanol and methanol.

14. The process of claim 4, wherein the alkene is a C2-C6 alkene selected from the group consisting of ethylene, propylene, and 1-butylene.

15. The process of claim 6, wherein the alkane containing gas is natural gas.

16. The process of claim 7, wherein the *Ralstonia* sp. strain is NCIMB 13287, the *Aneurinibacillus* sp. strain is NCIMB 13288 and the *Brevibacterium* sp. strain is NCIMB 13289.

17. The process of claim 8, wherein the carbon source is a carbohydrate selected from the group consisting of lactose and glucose.

18. The process of claim 11, wherein the bacteria culture is harvested between 5 and 24 hours after the start of the culture.

* * * * *